(12) United States Patent
Okuda et al.

(10) Patent No.: US 7,588,604 B2
(45) Date of Patent: Sep. 15, 2009

(54) PROSTHETIC LEG WITH KNEE BRAKING FUNCTION

(75) Inventors: Masahiko Okuda, Kobe (JP); Toyohiko Imakita, Kobe (JP); Aritomo Fukui, Kobe (JP); Yoshiaki Nakaya, Kobe (JP)

(73) Assignee: Nabco Limited, Hyogo (JP)

( * ) Notice: Subject to any disclaimer, the term of this patent is extended or adjusted under 35 U.S.C. 154(b) by 566 days.

(21) Appl. No.: 10/505,699

(22) PCT Filed: Nov. 19, 2003

(86) PCT No.: PCT/JP03/14713

§ 371 (c)(1),
(2), (4) Date: Aug. 23, 2004

(87) PCT Pub. No.: WO2004/045470

PCT Pub. Date: Jun. 3, 2004

(65) Prior Publication Data

US 2005/0234562 A1    Oct. 20, 2005

(30) Foreign Application Priority Data

Nov. 21, 2002  (JP)  ............................. 2002-338626
Nov. 21, 2002  (JP)  ............................. 2002-338628

(51) Int. Cl.
*A61F 2/64* (2006.01)
(52) U.S. Cl. ........................................................ 623/44
(58) Field of Classification Search .................. 623/43, 623/44, 45
See application file for complete search history.

(56) References Cited

U.S. PATENT DOCUMENTS 2,530,286 A    11/1950  Catranis
2,568,053 A     9/1951  Catranis (Continued)

FOREIGN PATENT DOCUMENTS

EP    0 503 775 A1    9/1992

(Continued)

*Primary Examiner*—William H. Matthews
(74) *Attorney, Agent, or Firm*—Frommer Lawrence & Haug LLP; Ronald R Santucci

(57) ABSTRACT

There is provided a prosthetic limb having a flexible knee brake function, which is designed such that it can be mechanically detected which part of the foot the load of the wearer is imposed on. In a thigh prosthetic limb (10), a joint upper member (12) including a knee plate (120) and a joint lower member (14) including a base bracket (22) integral with the frame (140) are operated to bend the knee. In the housing member (24), there are provided not only a knee axis but also a hydraulic brake circuit. There is a link mechanism (50) which allows a small relative motion between the housing member (24) and the base bracket (22) on the main body part side. The link mechanism (50) has an instantaneous center between the toe and the heel part of the prosthetic limb. This instantaneous center serves as a sensing point and detects which part of the foot the load of the wearer is imposed on by distinguishing a first case in which the wearer's load is imposed on the heel and a second case in which the wearer's load is imposed on the toe. Based on the detection result made by the link mechanism (50), the hydraulic brake circuit is controlled so that a flexible knee braking operation can be made.

15 Claims, 16 Drawing Sheets

U.S. PATENT DOCUMENTS

| | | | |
|---|---|---|---|
| 2,667,644 A * | 2/1954 | Johnson | 623/26 |
| 3,823,424 A * | 7/1974 | May | 623/39 |
| 3,863,274 A | 2/1975 | Glabiszewski | |
| 3,901,223 A * | 8/1975 | May | 602/16 |
| 4,351,070 A * | 9/1982 | Blatchford | 623/44 |
| 5,405,407 A | 4/1995 | Kodama et al. | |
| 5,405,409 A * | 4/1995 | Knoth | 623/44 |
| 5,704,945 A * | 1/1998 | Wagner et al. | 623/44 |
| 5,746,774 A * | 5/1998 | Kramer et al. | 623/39 |
| 5,888,237 A * | 3/1999 | Shiraishi et al. | 623/44 |
| 5,895,430 A * | 4/1999 | O'Connor | 623/39 |
| 5,948,021 A * | 9/1999 | Radcliffe | 623/44 |
| 6,086,616 A * | 7/2000 | Okuda et al. | 623/44 |
| 6,508,843 B2 * | 1/2003 | Suzuki | 623/46 |
| 2003/0195637 A1 * | 10/2003 | Shen | 623/44 |
| 2005/0015156 A1 * | 1/2005 | Hikichi | 623/24 |
| 2005/0038523 A1 * | 2/2005 | Cheng | 623/44 |
| 2006/0224248 A1 * | 10/2006 | Lang | 623/26 |

FOREIGN PATENT DOCUMENTS

| | | |
|---|---|---|
| JP | H 09-000551 | 1/1997 |
| WO | WO 00/38599 | 7/2000 |

* cited by examiner

PROSTHETIC LEG WITH KNEE BRAKING FUNCTION

This application is a 371 of PCT/JP2003/014713 filed on Nov. 19, 2003, published on Jun. 3, 2004 under publication number WO 2004/045470 A1 which claims priority benefits from Japanese Patent Application Number 2002-338626 filed Nov. 21, 2002 and Japanese Patent Application Number 2002-338628 filed Nov. 21, 2002.

TECHNICAL FIELD

This invention relates to a prosthetic limb including a knee joint which makes it possible for its user to bend the knee, the prosthetic limb flexibly braking the bending motion of the knee, i.e., a yielding prosthetic limb, and more particularly to a prosthetic limb in which a sensing part capable of detecting which part of the prosthetic limb, the load of its wearer is imposed on comprises a mechanical link mechanism.

BACKGROUND ART

For those who need to wear a prosthetic limb, it is a fundamental desire to walk naturally in the same way as healthy persons do. Particularly, it is a desire, almost like a dream, for them to walk up and down steps and/or walk down a downhill smoothly by moving the left and right feet alternately. A flexible knee braking function, namely, yielding function is a function for realizing the latter desire of those who need to wear a prosthetic limb. Owing to this yielding function, the knee joint is slowly changed in bending angle when the wearer's load is imposed on the prosthetic limb including a knee joint. Therefore, the wearer of the prosthetic limb having such a yielding function can smoothly walk down steps and a downhill by placing his/her weight on the prosthetic limb with confidence and moving the left and right limbs alternately.

From another view point, it can be said that the yielding technique is a technique for flexibly locking the prosthetic limb in a bendable condition compared with a technique for completely locking the prosthetic limb (bending motion of the prosthetic limb). The technique for completely locking the prosthetic limb is a technique for producing a braking force by tightening a knee axis by utilizing a mechanical friction force, as shown, for example, in U.S. Pat. No. 3,863,274 (corresponding to Japanese Patent Publication No. Sho 52-46432). In contrast, the technique for flexibly locking the prosthetic limb is a technique for producing a braking force by utilizing a flow resistance generated when a working oil or fluid passes through a throttle. Therefore, the flexible lock mechanism comprises a hydraulic brake circuit including several hydraulic equipments, besides the throttle. One of the hydraulic equipments included in the hydraulic brake circuit is means for defining two chambers into which or from which the working fluid flows. Known as the means are a piston type including a reciprocally movable piston and a rotary type including a turnable vane. U.S. Pat. No. 5,704,945 (corresponding to Japanese Patent Application Laid-Open No. H08-317944), U.S. Pat. No. 2,667,644, etc. disclose the rotary type, and U.S. Pat. No. 2,530,286, U.S. Pat. No. 2,568,053, etc. disclose the piston type.

PROBLEMS TO BE SOLVED BY THE INVENTION

A hydraulic brake circuit normally includes a switch valve (i.e., control valve) for selectively switching between a braking position for producing a braking force with respect to the bending motion of the knee and a non-braking position for canceling the braking force. And the hydraulic brake circuit (i.e., switch valve for the hydraulic brake circuit) is controlled depending on which part of the foot attached to the prosthetic limb the weight of the wearer is imposed on. As sensing control means for controlling the hydraulic brake circuit in such a manner, it is accepted that a walking mode of the wearer is detected by an electric sensor such as a strain gage and a control signal is outputted from a microcomputer in accordance with the detection signal. That is, controlling can also be made totally in such a manner as to detect and process electrically or electronically. However, since data processing must be done using a microcomputer for that purpose, it is necessary to prepare a power source for it. Moreover, the electric sensor must be maintained always in a detectable condition. This means to consume electric power to that extent. In order to solve those problems, it is preferable that the sensing control means is constituted mechanically.

However, none of the conventional sensing control means using a mechanical method is made based on such a design concept enabling to detect which part of the foot the load of the wearer is imposed on as in the above-mentioned electric or electronic method. For example, in U.S. Pat. Nos. 2,530,286 and 2,667,644, the foot and the switch valve of the hydraulic brake circuit are connected to each other through the link mechanism, and the switch valve is controlled by the link mechanism interlocked to motion of the foot. Also, there is another one in which the switch valve of the hydraulic brake circuit is controlled solely depending on whether or not the prosthetic limb is bent, irrespective of whether or not the foot is bent. That is, in U.S. Pat. No. 5,704,945 (corresponding to Japanese Patent Application Laid-Open No. H08-317944), relative displacement of a turnable lever caused by bending motion of the knee is utilized for controlling operation, while in U.S. Pat. No. 2,568,053, motion of a link and a lever caused by bending motion of the knee is utilized for controlling operation.

However, the conventional technique adopting a mechanical method has the following problem. Since it is not of the type capable of detecting which part of the foot the load of the wearer is imposed on, braking force is not correctly canceled at the time for departing the toe in the final stage of the stance phase in case the wearer tries to walk down steps or downhill. This makes it difficult for the wearer to smoothly shift the walking phase into the swing phase. The reasons are as follows. When the wearer walks down steps or downhill, he/her tends to place the center of gravity comparatively backward. Therefore, the floor reaction force passes through a rather rear part of the knee axis. That is, in case of walking on a flat ground or floor, the switch valve of the hydraulic brake circuit can be switched effectively in such a manner as to interlock to the motion of the foot or motion in association with the bending motion of the knee. In contrast, in case the wearer walks down steps or downhill, it is almost impossible for him/her to make such a switching operation correctly due to the attitude of the wearer.

It is therefore, an object of the present invention to provide a prosthetic limb having a flexible braking function, which is capable of mechanically detecting which part of the foot the load of the wearer is imposed on.

Another object of the present invention is to provide a prosthetic limb having a flexible braking function, which is capable of correctly canceling braking force at the time the toe is departed from the floor in the last stage of the stance phase.

A further object of the present invention is to provide a prosthetic limb having a flexible braking function, which can be applied not only to a prosthetic limb having a single axis but also to a prosthetic limb having a multi-axis.

A still further object of the present invention is to provide a prosthetic limb, which is capable of positively producing a desired braking force when a predetermined load is imposed, in order to ensure safety of the flexible knee braking function.

A yet further object of the present invention is to provide a prosthetic limb, in which the flexible knee braking function in a stance phase and controlling in a swing phase are compatible.

An additional object of the present invention is to provide a prosthetic limb, in which the wearer can impose the load on the knee with a confidence and the knee can be bent by his/her own will.

Further specific objects of the present invention will become manifest from the description to be followed.

DISCLOSURE OF THE INVENTION

A prosthetic limb according to this invention is a technique capable of flexibly braking the prosthetic limb in a bendable condition, and it includes a hydraulic brake circuit (i.e., knee brake circuit operated by hydraulic) for producing a braking force by utilizing a flow resistance generated at the time the working hydraulic passes through a throttle. As a throttle in a hydraulic brake circuit, any of a variable throttle and a fixed throttle can be used. From a view point of making it possible to adjust a throttling amount in accordance with characteristic and preference of the wearer, however, the variable throttle is preferable. The throttle is operated to apply resistance to the working fluid flow passing therethrough so that the knee can be bent flexibly. The bending resistance is sufficient if the knee can be bent slowly when the own load (weight) of the wearer is imposed on the prosthetic limb. For example, it may be in the range of from 40 to 100 Nm. In order to generate such a braking function by the throttle only when the knee is bent, in other words, in order not to generate such a braking function by the throttle when the knee is extended, the knee brake circuit is, of course, provided with a check valve which is arranged in parallel with the throttle. As a check valve, a simple valve of the type in which a ball or poppet serves as a valve body is preferably used.

The hydraulic brake circuit includes, in addition to the throttle and the check valve, means for defining two chambers into which or from which working fluid flows, and a switch valve capable of switching between a braking position and a non-braking position. As means for defining two chambers, there are two types, as already mentioned above, one being a piston type including a reciprocally movable piston and the other being a rotary type including a turnable vane. Any of those two types can be applied to the present invention. However, in view of making the prosthetic limb small and effectively making coexistence of the hydraulic brake circuit for obtaining a flexible knee braking function in the stance phase and the air cylinder for controlling the bending motion of the knee in the swing phase, the rotary type is more preferable. Owing to the hydraulic brake circuit, there can be obtained not only the flexible knee braking function in the stance phase but also the controlling of the bending motion of the knee in the swing phase.

The switch valve is a valve which is opened/closed upon receipt of load of the wearer, and it performs a switching function in which switching is made between an open position and a closed position. In the knee brake circuit, the switch valve in the closed position shuts off the flow of the working fluid to make it effective of the throttling function, and the switch valve in the open position allows the working fluid smoothly to make it meaningless or ineffective of the throttling function. Accordingly, as a switch valve, a switch is preferable which has such a structure that the valve can be switched between an open position and a closed position by a small number of strokes. A particularly preferable valve is a seat valve in which a valve body is urged against a valve seat to open/close the valve. In the seat valve, the valve body is moved in the orthogonal direction with respect to the plane of the valve seat at the time the valve is opened/closed. In such a valve, by a small motion of the valve body, a ring-shaped opening having a height equal to that movement is formed. Accordingly, a large area of a flow passageway can instantaneously be obtained. It is most preferable that the valve body and the valve seat of the switch valve are surface contacted with each other in order to reliably and rapidly perform the switching operation of the switch valve.

This invention can widely be applied to a prosthetic limb comprising a joint upper member located at an upper side of the knee, and a joint lower member located at a lower side of the knee and pivotably connected to the joint upper member so that the knee can be bent. As means for pivotably connecting the joint upper member and the joint lower member together, there are known means for connection by means of a single-axis or by means of a multi-axis using plural axes such as four axes. The present invention can be applied to any one of them. Since this invention intends to obtain a flexible knee braking function chiefly by mechanical means, the joint lower member of the prosthetic limb comprises two parts which can be moved relative to each other. Specifically, the joint lower member comprises a joint component part composing the knee joint which is connected to the joint upper member such that the knee can be bent, and a main body part connected to the lower side of the joint component part and moving only slightly, when compared with the motion of the knee, with respect to the joint component part. The joint component part is located at an upper part of the main body part, and a foot is located at a lower part of the main body part.

In a preferred form of the present invention, the hydraulic brake circuit is disposed at the joint component part of the joint lower member, and a rotary type means including a turnable vane is employed as means for defining two chambers in the hydraulic brake circuit.

This invention further comprises a specific sensing control means for detecting, in order to control the hydraulic brake circuit for producing a braking force with respect to the bending motion of the knee, which part of the foot the load of the wearer is imposed on and control the hydraulic brake circuit in accordance with the detection signal. The sensing control means has the following constitutional features y1 and y2, y1. a link mechanism for connecting the joint component part and the main body part to each other in the joint lower member and having an instantaneous center between the toe and the heel of a foot of the prosthetic limb, and y2. motion of a link constituting the link mechanism being detected and the hydraulic brake circuit being controlled based on the detection result.

The sensing control means includes a sensing part for detecting which part of the foot the load of the wearer is imposed on, and a control part for controlling the hydraulic brake circuit in accordance with the detection signal coming from the sensing part. The sensing part comprises the above-mentioned predetermined link mechanism, and the instantaneous center of the link mechanism serves as a sensing point. Depending on the grounding condition (whether the heel is contacted with the floor or the toe is contacted with the floor) of the prosthetic limb, the following detection signal z1 or z2 is generated, z1. when the heel of the foot of the prosthetic limb is contacted with the floor, a floor reaction force caused by grounding of the heel passes through the rear side of the instantaneous center of the link mechanism, thereby generating a rotational moment to the joint lower member in a forwardly folding direction about the instantaneous center, and z2. when the toe of the foot of the prosthetic limb is contacted with the floor, a floor reaction force caused by grounding of the toe passes through the front side of the instantaneous center of the link mechanism, thereby generating a rotational moment to the joint lower member in a backwardly folding direction about the instantaneous center.

That is, depending on whether the load of the wearer is imposed on the heel or toe of the foot, the mechanical link mechanism produces mutually different two rotational moments, one being folded forward about the instantaneous center and the other being folded backward. Those mutually different rotational moments serve as detection signal detected by the link mechanism. In accordance with the detection signal detected by the link mechanism (i.e., sensing part), the hydraulic brake circuit is controllingly switched between a braking position and a non-braking position. This controllingly switching operation generally refers to a controllingly opening/closing operation to be made with respect to the switch valve in accordance with motion of one link of the link mechanism. It should be noted, however, that the controllingly switching operation is not limited to the above. For example, it is also accepted that an electric switch is switched in accordance with the motion of a link of the link mechanism and the throttling amount of the variable throttle is controlled by a motor or the like in accordance with the switching action. Accordingly, although detection made by the sensing part is the mechanical, controlling of the hydraulic brake circuit by a control part is not limited to the mechanical. Instead, it may include the electric or electronic.

The mechanical link mechanism has an instantaneous center between the toe and the heel of the foot of the prosthetic limb. The instantaneous center is preferably in a region below the link mechanism and at a forward region from a loading line passing through the center of gravity of the wearer in a standing position. If the instantaneous center is in the above-mentioned region, the braking force can surely be produced in a standing position and the braking force can effectively be canceled at the time the toe is departed from the floor on a downhill. Thus, there can be obtained a prosthetic limb of high stability.

The switch valve of the hydraulic brake circuit may be either of the normally open type or of the normally closed type. In view of surely preventing the knee from folding by reliably applying a braking function at normal times, however, the normal closed type is preferable. Moreover, in case controlling in the swing phase is made by an air cylinder apparatus other than the hydraulic brake circuit, it is preferable that the switch valve is normally closed and the instantaneous center of the link mechanism is located at a relatively lower part in the vicinity of the foot. By doing so, the force acting for opening the switch valve is increased due to force of inertia of the prosthetic limb caused by the swinging out action even after the toe is departed from the floor and the walking phase is shifted into the swing phase. Moreover, a reaction force of the air cylinder apparatus is additionally applied. Thus, the switch valve can be opened and controlling in the swing phase can be executed smoothly. As a countermeasure for opening the switch valve at the time the walking phase is shifted into the swing phase, a spring force for applying a sitting force to the valve body so as to sit on the valve seat can be invalidated when the prosthetic limb is contacted to the floor at the toe, for example. In the conventional hydraulic brake circuit, the switch valve and the throttle are composed of a valve apparatus which is placed at an intermediate part of the passageway. This arrangement may be employed into the present invention. In view of surely exhibiting the flexible knee braking function, however, it is preferable that the switch valve and the throttle are separated and connected to a check valve in parallel. By arranging the hydraulic brake circuit in that way, the switch valve can surely be switched when a predetermined load is applied to the prosthetic limb irrespective of the size and direction of the load. This makes it possible to stably produce a predetermined braking force. Accordingly, the wearer can freely control the knee braking force in the way he/or she wants.

BEST MODE FOR CARRYING OUT THE INVENTION

Figure 1:
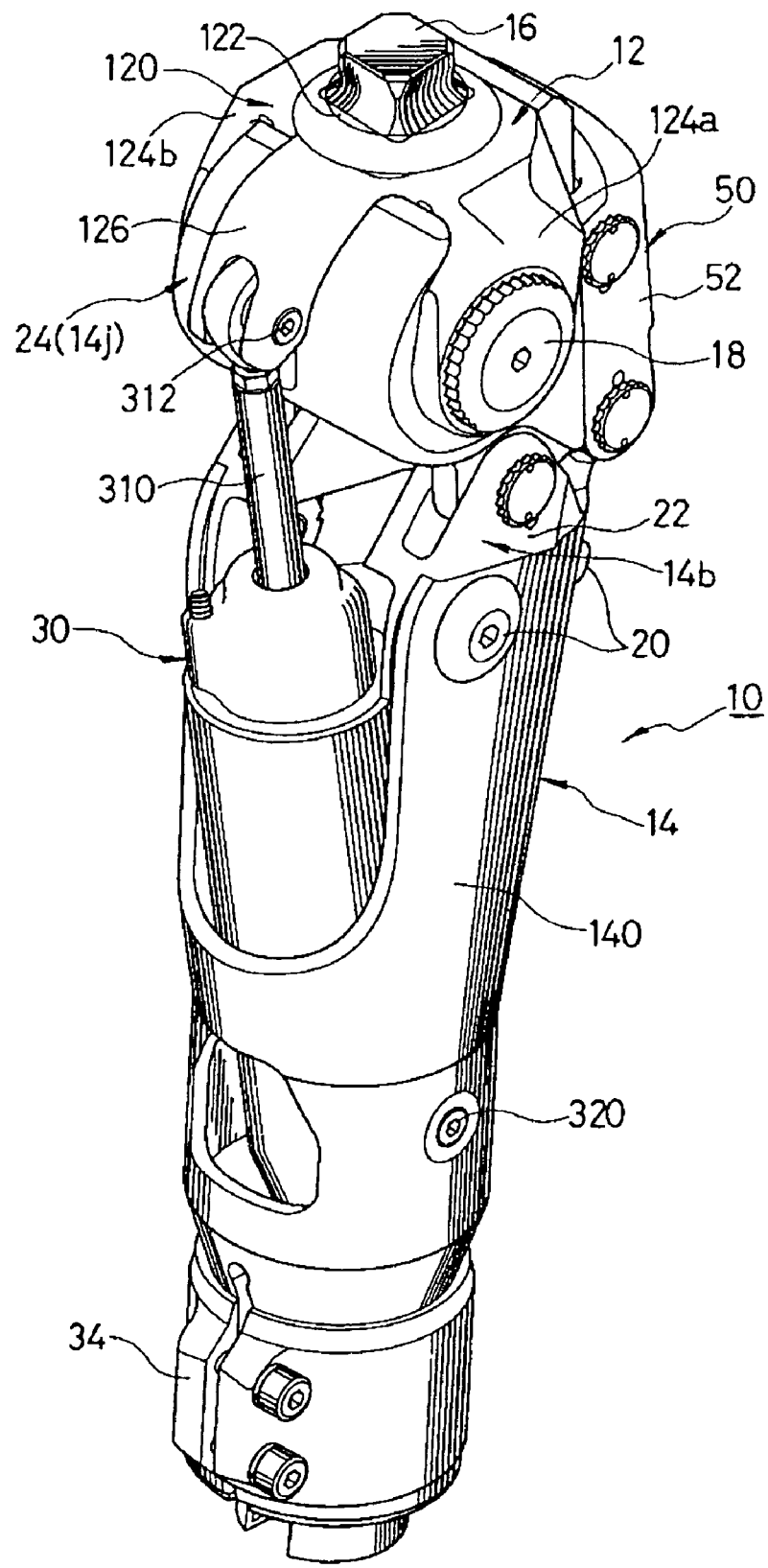
FIG. 1 is a perspective view showing one embodiment of a prosthetic limb according to the present invention.
Figure 2:
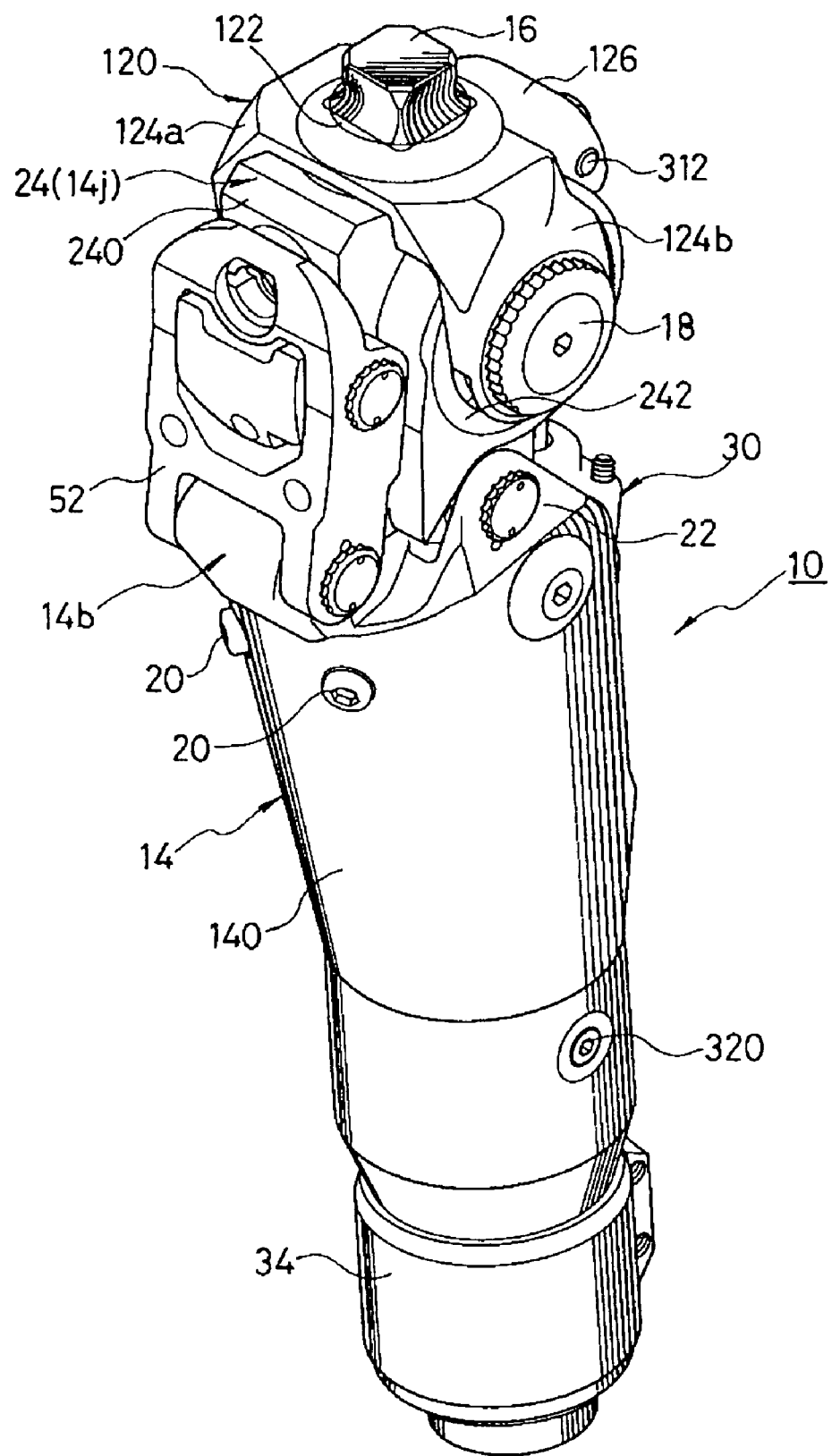
FIG. 2 is a perspective view, when viewed from the opposite side, of the embodiment of FIG. 1.
Figure 3:
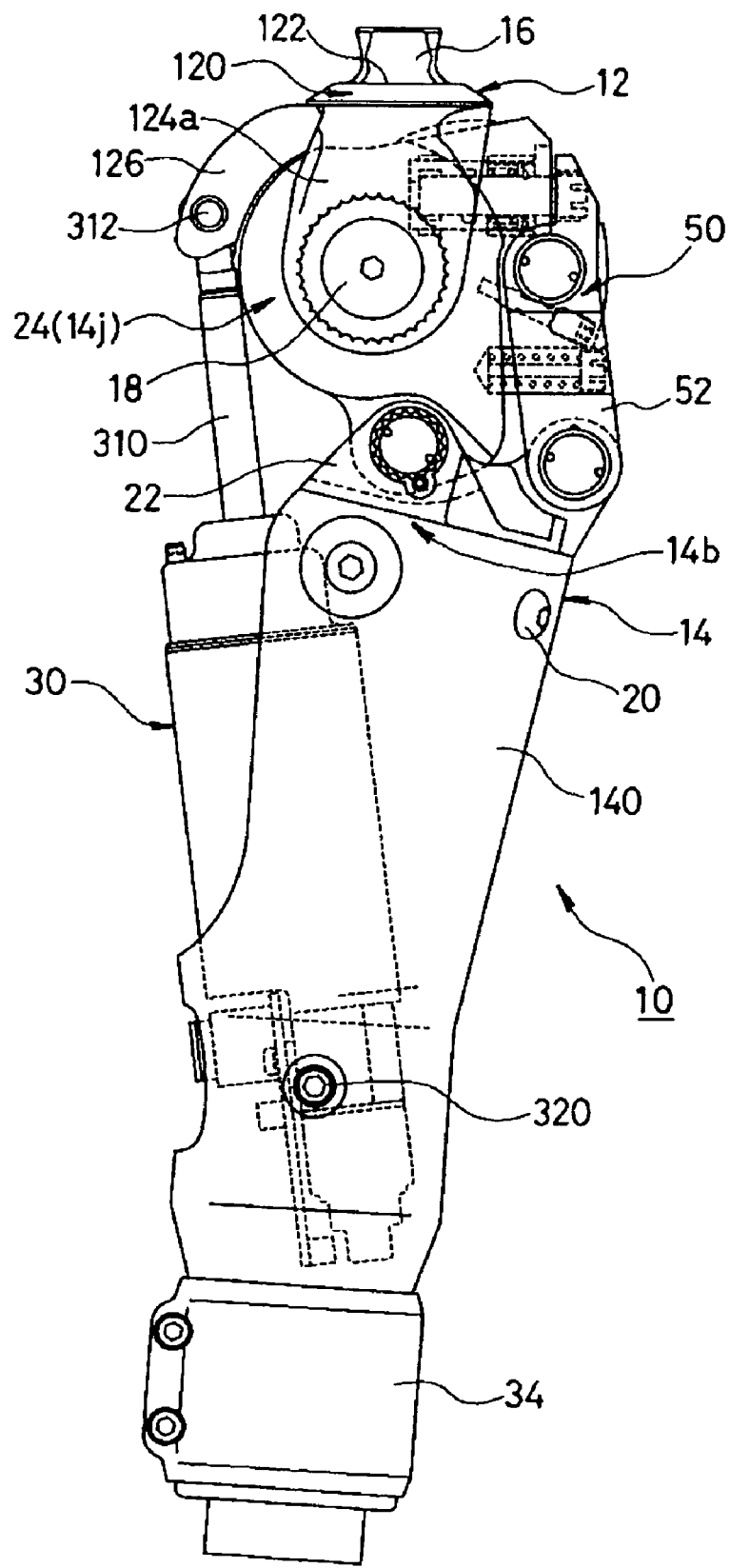
FIG. 3 is a front view of the embodiment of FIG. 1.

FIGS. 1 through 3 illustrate an overall construction of a thigh prosthesis 10 to which the present invention is applied. First, the construction of a thigh prosthesis 10 and the features of the present invention contained therein will be described with reference to those Figures.

The thigh prosthesis 10 is a prosthetic limb for those who have no knee. This thigh prosthesis 10 includes a joint upper member 12 located at an upper side of the knee and a joint lower member 14 located at lower side of the knee and pivotably connected to the joint upper member 12 so that the knee can be bent. A main component of the joint upper member 12 is a knee plate 120 which is made of aluminum alloy. The knee plate 120 is provided with a part 122 located at an upper part thereof and adapted to support an alignment block 16, a pair of arms 124a, 124b located at left and right sides thereof and adapted to support a knee axis, and a third arm 126 located between the arms 124a, 124b. The alignment block 16 is made of, for example, titanium alloy and fixedly screwed to the knee plate 120. The alignment block 16 supports a socket, not shown, and bears the wearer's load through the thigh which is inserted in the socket.

The knee axis (not shown) is integrally fixed to the knee plate 120 (thus, to the joint upper member 12) by toothed check bolts 18 which are bolted into opposite sides of the knee plate 120. The thigh prosthesis 10 is a single-axis prosthetic limb which has a single (only one) knee axis. The joint upper member 12 and the joint lower member 14 are rotatable about the single knee axis.

The joint lower member 14 is provided with a hollow frame 140 which is made of carbon fiber-reinforced plastic, and some other component members such as a base bracket 22 which is fixed to an upper part of the frame 140 by a plurality of check bolts 20 and a housing member 24 which is rotatably connected to the knee axis and further connected to the base bracket 22 through a specific link mechanism (later described). The base bracket 22 and the housing member 24 are each made of aluminum alloy. The housing member 24, which is rotatably about the knee axis, is a joint component part which composes a knee joint through which the knee can be bent. Accordingly, the housing member 24 as a joint component part can be rotated or pivoted at such a large angle as, for example, 150 degrees to 160 degrees with respect to the joint upper member 12 including the knee plate 120. The housing member 24 is also a part composing a hydraulic brake circuit which produces a braking force with respect to the bending motion of the knee. The housing member 24 comprises a main body 240 having cylinder holes formed in opposite sides and for defining an internal space for retaining hydraulic, and closing cover members 242 located at opposite sides of the main body 240 and for closing the opening of the cylinder hole.

The hydraulic brake circuit in the housing member 24 is to obtain a knee braking function (controlling in a stance phase) related to the present invention. The thigh prosthesis 10 further includes an air cylinder unit 30 operated by pneumatic. This air cylinder unit 30 serves as walking auxiliary means in a swing phase. This air cylinder unit 30 itself is known per se. For example, it is of the same type as those which are disclosed in U.S. Pat. No. 5,405,407, Japanese Patent Application Laid-Open Publication No. H09-551, U.S. Pat. No. 5,888,237 or the like. Controlling by the air cylinder unit 30 is common with that of hydraulic in using of flow resistance which is generated when the fluid passes through the throttle. However, since air as fluid is compressive, according to the air cylinder unit 30, there can be obtained a reaction force by compression energy generated by compression of air after the knee is bent maximum. The thigh prosthesis 10 is a prosthetic limb which is capable of achieving the controlling by hydraulic in the stance phase and by pneumatic in the swing phase. The air cylinder unit 30 is rotatably supported at one end thereof on the rod 310 side by the arm 126 through a clevis pin 312 and at another end on the cylinder bottom side by a trunnion pin 320 which is fixed to the frame 140. A sectionally C-type ring-shaped tightening member 34 which is located at a lower part of the frame 140 is adapted to connect a foot pipe to the frame 140. A lower end of the foot pipe is, of course, attached with a foot-shaped foot.

In the thigh prosthesis 10 constructed in the manner as mentioned above, according to the present invention, a joint component part 14j (housing member 24) of the joint lower side member 14 and a main body part 14b) part including the frame 140 and a base bracket 22 which is integral with the frame 140) which is located at a lower part of the joint component part are connected to each other by a specific link mechanism 50. The link mechanism 50 allows a small relative motion between the housing member 24 as a joint component part and the base bracket 22 on the main body part. The link mechanism 50 has an instantaneous center between the toe and the heel of the foot of the thigh prosthesis 10. The expression "small motion" refers to a very small pivoting motion at an angle of 3 degrees or less, for example. This expression is in contrast of the above-mentioned large motion at an angle of ranging from 150 degrees to 160 degrees about the knee axis. The "small motion" also refers to such a motion small enough not to give a sense of uneasiness or disorder to the wearer. The link mechanism 50 is a mechanical construction and it has an instantaneous center outside the component element thereof. The instantaneous center serves as a sensing point which makes it possible to distinguish between a case in which the load of the wearer is imposed on the heel of the foot and another case in which the load of the wearer is imposed on the toe. Based on the detection result, the link mechanism 50 controls the hydraulic brake circuit. In this invention, it is detected which part of the foot the load of the wearer is imposed on by serving, as a sensing point, the instantaneous center located at a predetermined region outside the link mechanism 50 which composes the sensing part. Owing to this feature, correct detection can always be obtained irrespective of the walking attitude of the wearer, not only at the time the wearer is walking on a flat land but also at the time the wearer is walking down steps and a downhill. And based on this detection the hydraulic brake circuit can properly be controlled and a flexible knee braking function can be obtained.

Figure 4A:
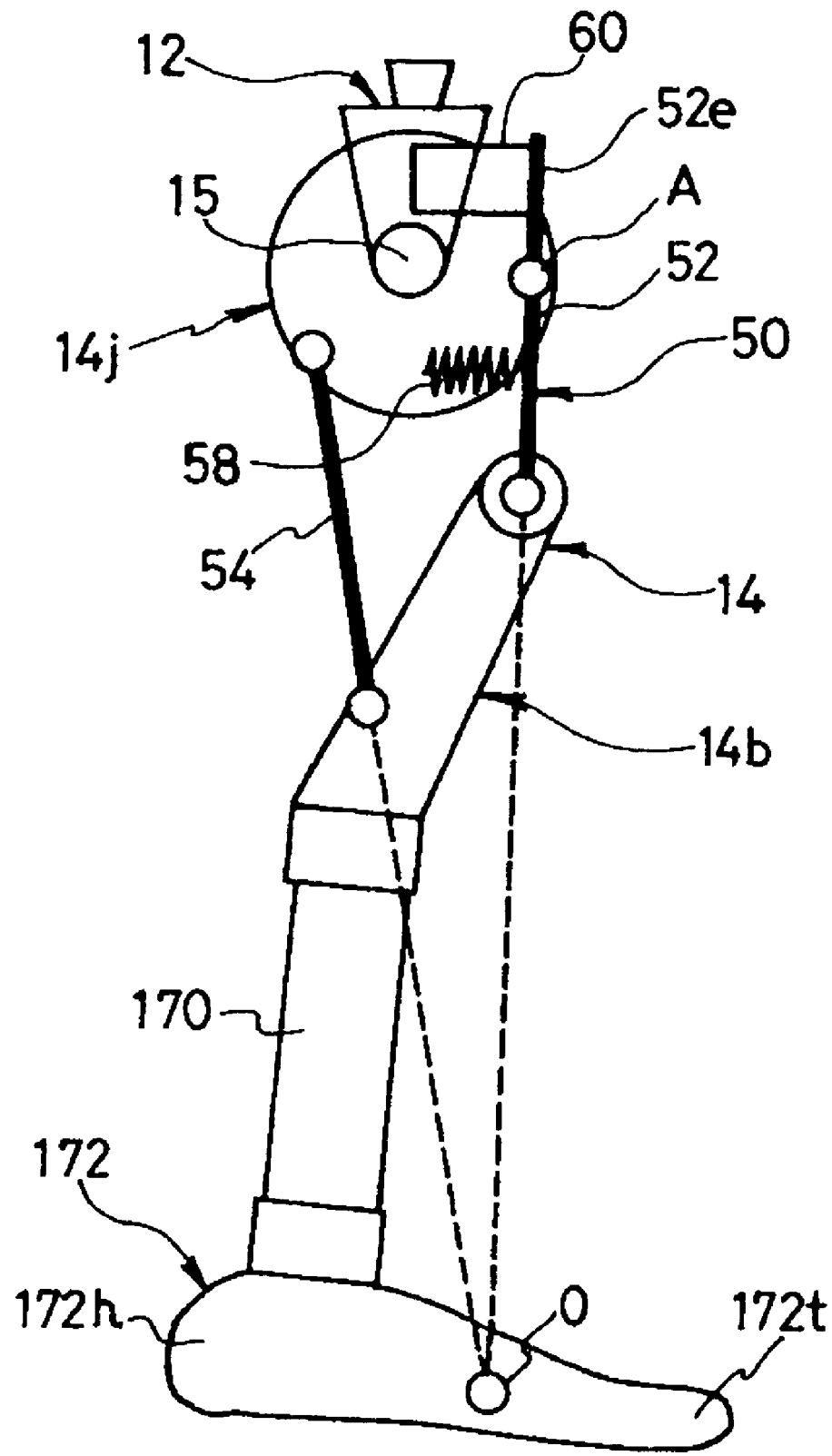
FIG. 4A is a view showing one example of the prosthetic limb according to the present invention in the form of a skeleton.
Figure 4B:
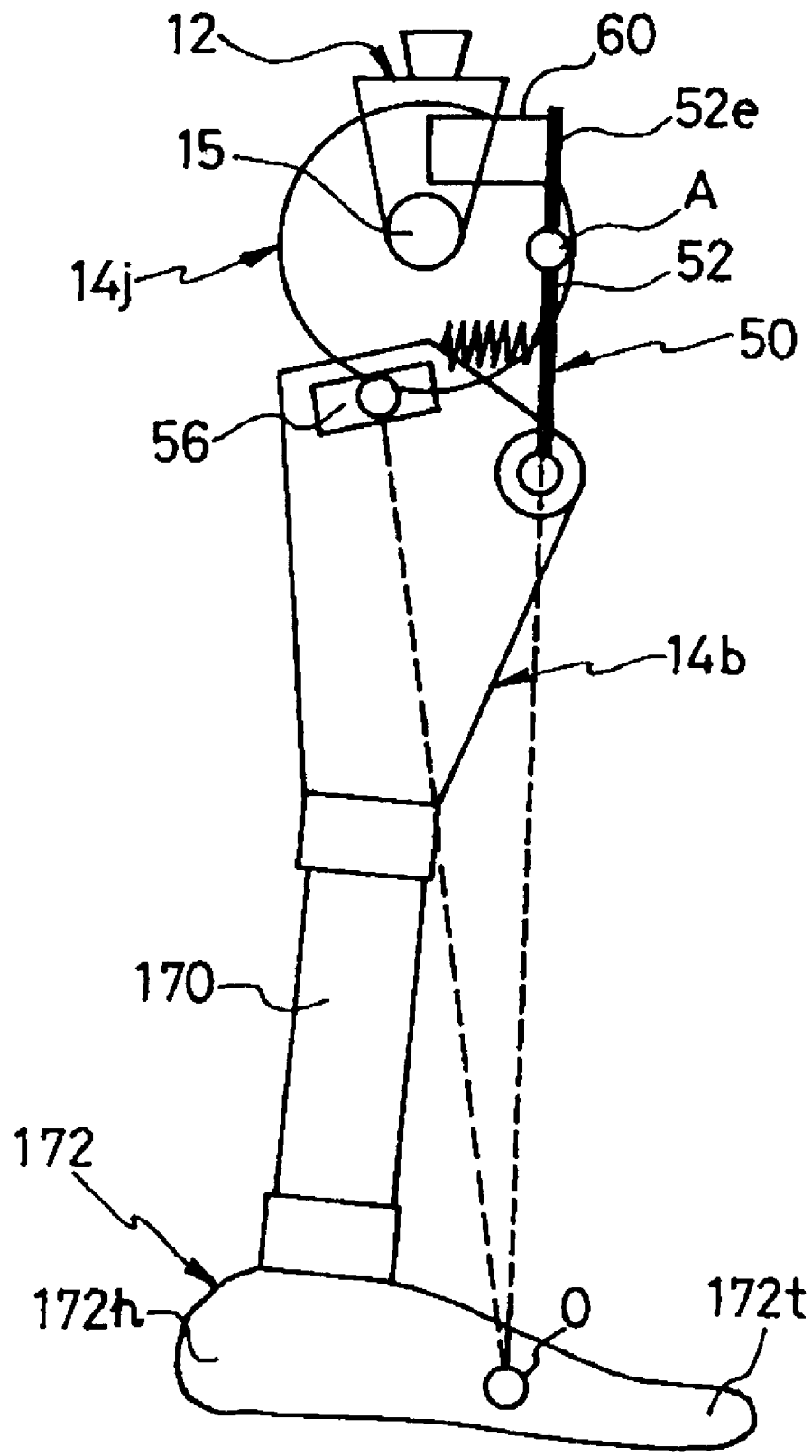
FIG. 4B is a skeleton view in which a part of a link of FIG. 4A is formed of a slide.

FIGS. 4A and 4B show the link mechanism 50 in the form of a skeleton. FIG. 4A is an example in which a bar link is used, and FIG. 4B is another example in which a part of the bar link is replaced with a slide. Both of them are equivalent as a link mechanism. In those two examples, the knee axis 15 rotatably interconnect the joint upper member 12 and the joint lower member 14. A foot 172 is attached to a lower part of the joint lower member 14 through a foot pipe 170. In FIG. 4A, a front link 52 and a rear link 54 are pivotally connected between the joint component part 14j and a main body part 14b of the joint lower member 14. Owing to this arrangement, the link mechanism 50 of FIG. 4A comprises, besides the joint component part 14j and the main body part 14b, the front link 52 and the rear link 54. In the link mechanism 50 of FIG.

4B, a mechanically equivalent slide 56 is used instead of the rear link 54. Those link mechanisms 50 have an instantaneous center at a point O between the toe 172t and the heel 172h of the foot 172.

Figure 5A:
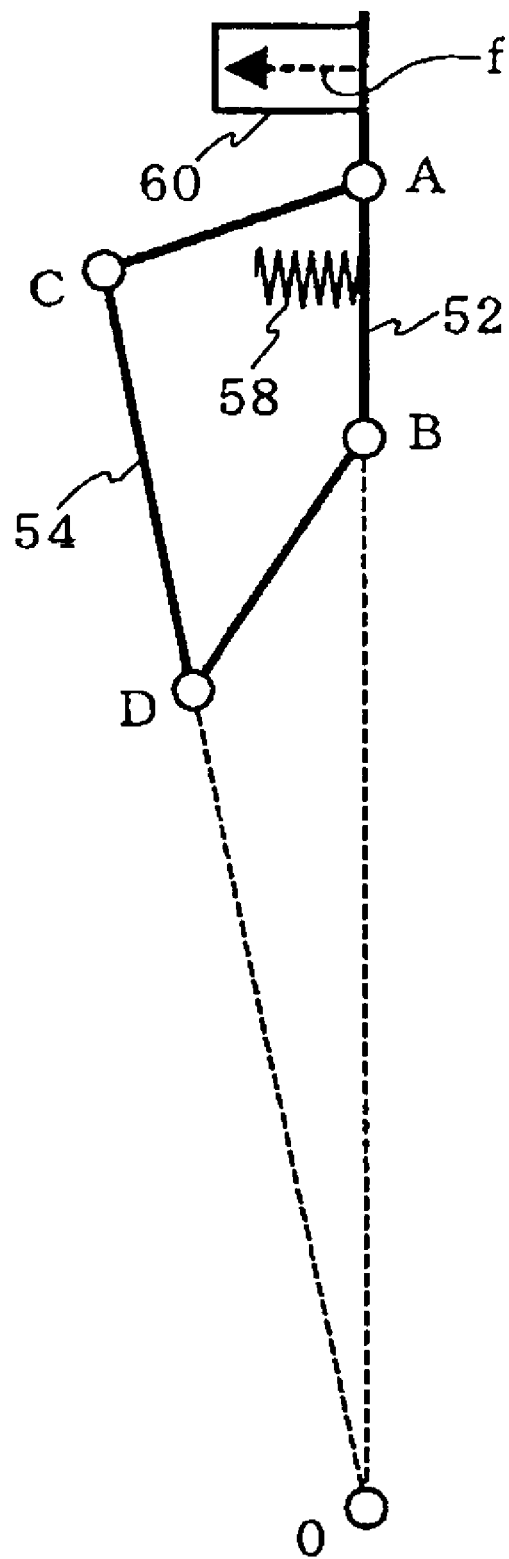
FIG. 5A is a view showing the operation of a link mechanism which is used in the present invention when it is in a normal condition.
Figure 5B:
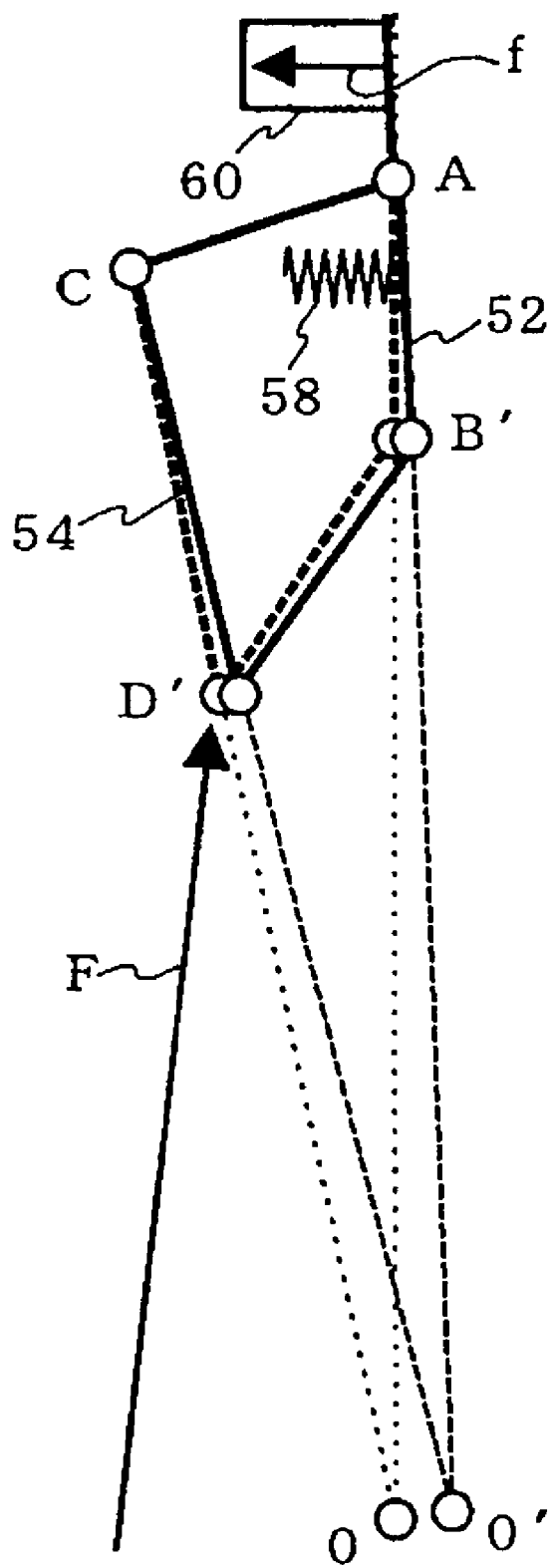
FIG. 5B is a view showing the operation of a link mechanism which is used in the present invention when the wearer's heel is in contact with the floor.
Figure 5C:
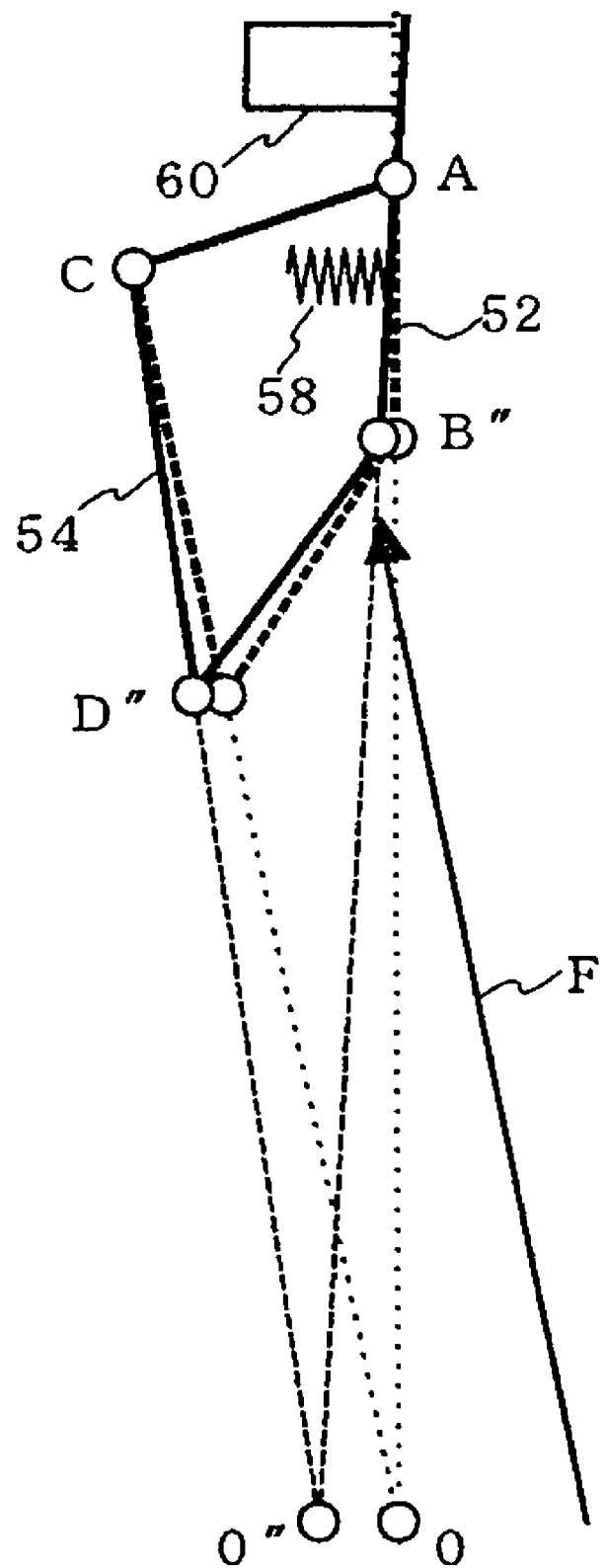
FIG. 5C is a view showing the operation of a link mechanism which is used in the present invention when the toe is in contact with the floor.

The front link 52 of the link mechanism 50 serves as a pivot connection part A at an intermediate part thereof in the axial direction with respect to the joint component part 14j side. A part 52e at an end of the link from the pivot connection part A serves as an operating element of the switch valve 60 of the hydraulic brake circuit. In this example, a spring 58 composed of a compression spring is disposed at the opposite side to the part 52e of the front link 52 in order to normally close the switch valve 60. FIGS. 5A and 5B show the action of the link mechanism 50. The link mechanism 50 is a quadratic link mechanism having a pivot joint part at four points A, B, C and D. The instantaneous center O of the link mechanism 50 is an intersection between a straight line connecting the pivot joint part A and B of the front link 52 and a straight line connecting the pivot joint part C and D of the rear link 4. In a normal state, force of the spring 58 acts on the front link 52. As a consequence, an operating force f acts on the switch valve 60 so that the switch valve 60 is closed to bring the prosthetic limb into a state in which the prosthetic limb is subjected to braking operation of the hydraulic brake circuit (see FIG. 5A). In case the floor reaction F acts on the heel 172h or heel 172h side of the foot 172, the floor reaction force F acts backward of the instantaneous center O. Accordingly, the link mechanism 50 is deformed such that the operating force f acts on the switch valve 60 as in the normal state (see FIG. 5B, link mechanism AB'CD' after deformed). In case the floor reaction force F acts on the toe 172t or toe 172t side of the foot 172, the floor reaction force F acts forward of the instantaneous center O. Accordingly, contrary to the preceding case, the link mechanism 50 is deformed such that the force of the spring 58 is offset to open the switch valve 60 so that the braking effect of the hydraulic brake circuit is canceled (see FIG. 5C, link mechanism AB" CD" after deformed).

Figure 6:
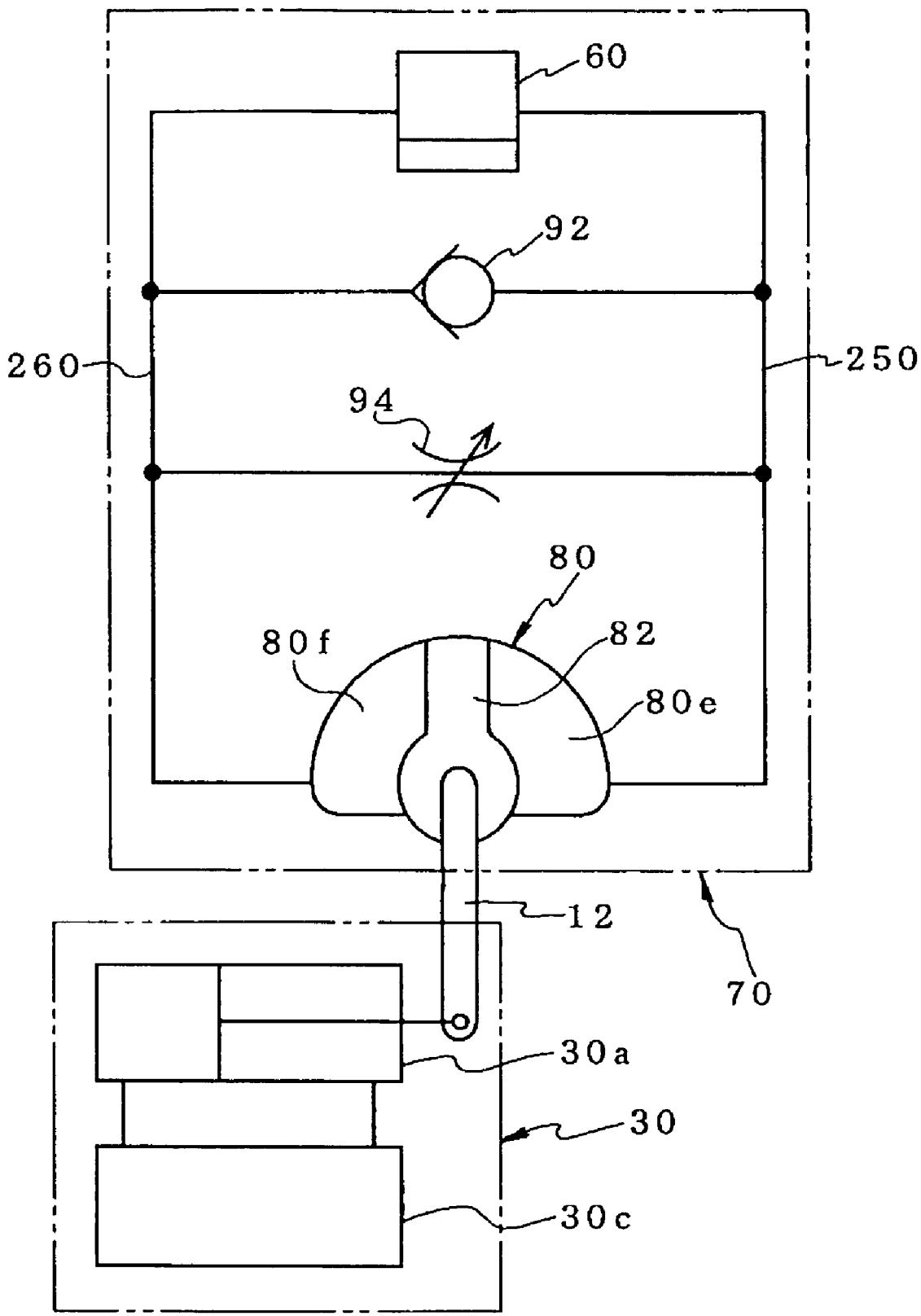
FIG. 6 is a circuit diagram showing one example of a hydraulic brake circuit which is used in the present invention.

Next, the hydraulic brake circuit including the switch valve 60 will be described. The thigh prosthetic limb 10, as shown in FIG. 6, comprises a hydraulic brake circuit 70 including the switch valve 60 and an air cylinder apparatus 30 including an air cylinder 30a and a pneumatic circuit 30c attached thereto. The prosthetic limb 10 including a combination circuit of the hydraulic and pneumatic can obtain a flexible knee braking function in the stance phase owing to the hydraulic brake circuit 70, and an auxiliary function of the bending motion and the extending motion of the knee in the swing phase owing to the air cylinder apparatus 30. As for the air cylinder apparatus 30, a known one can be employed. In the air cylinder 30a, a piston contained therein defines two chambers, one at the front side and the other at the rear side, in the axial direction of the piston. The pneumatic circuit 30c includes a throttle and a check valve and controls the flow of air flowing into and out of the front and rear chambers. The chamber defining means (i.e., air cylinder 30a) in the air cylinder apparatus 30 is of a piston type in which the piston is reciprocally moved in the axial direction. On the other hand, a chamber defining means 80 in the hydraulic brake circuit 70 is of a rotary type in which a turnable vane 82 defines two chambers 80e and 80f. The turnable vane 82 on the hydraulic brake circuit 70 side and the piston 30a on the air cylinder apparatus 30 side are connected to each other through the knee plate 12. Of the two chambers defined by the chamber defining means 80 of the hydraulic brake circuit 70, the first chamber 80e is an extending chamber and the second chamber 80f is a bending chamber. The extending chamber 80e is a chamber into which oil flows when the knee extends and out of which oil flows when the knee bends. On the other hand, the bending chamber 80f is a chamber into which oil flows when the knee bends and out of which oil flows when the knee extends. The extending chamber 80e is communicated with one side of the switch valve 60 through a first passageway 250, and the bending chamber 780f is communicated with the other side of the switch valve 60 through a second passageway 260. In order to smoothly flow the oil, the first passageway 250 or the second passageway 260 may be provided with an accumulator.

The hydraulic brake circuit 70 further includes a check valve 92 and a throttle (i.e., throttle valve) 94 in parallel with the switch valve 60 and the chamber defining means 80 between the first passageway 250 and the second passageway 260. The check valve 92 is a one-way valve for prohibiting the flow from the first passageway 250 side toward the second passageway 260 side (i.e., flow from the first chamber 80e toward the second chamber 80f) and allowing the flow in the opposite direction. The throttle 94 is a member for applying resistance to the flow passing therethrough. As this throttle 94, various types can be employed. Among them, those are preferable in which the throttling amount can easily be adjusted depending on the physical features, preference of the manner of walking of the wearer, etc. As one preferred example of the throttle 94, there can be listed a throttle in which axially slanted cutout grooves (for example, two cutout grooves are arranged in the peripheral direction at an interval of 180 degrees) are formed in the outer periphery of the valve body. The throttle 94 thus constructed can easily be adjusted in its throttling amount by screw adjustment so that it can appropriately be met with the characteristic of the wearer.

In the hydraulic brake circuit 70, any of the normally open and the normally closed type can be applied to the switch valve 60. In this embodiment, the normally closed switch valve 60 is employed. By employing the normally closed type, the braking function caused by the throttle 94 can always work efficiently at normal times so that the knee can be prevented from being folded. In such a normal condition, the flow resistance caused by the throttle 94 is equivalent to, for example, 40 to 100 Nm and the wearer of the prosthetic limb equipped with the knee brake circuit 70 can slowly bend the knee by placing his/her weight onto the knee. Moreover, since the knee brake circuit 70 is designed such that a braking force is produced by the flow resistance caused by throttle 94 which is provided separately from the switch valve 60, the wearer can surely and rapidly execute the opening/closing controlling operation of the switch valve 60 by placing his/her own weight onto the prosthetic limb. The reason why is as follows. In the switch valve 60, when a predetermined load is imposed on the prosthetic limb, a plunger 610 is actuated, and slight movement of the plunger 610 generates a ring-like large opening. The switch valve 60 keeps its closed state when the walking phase is shifted from the swing phase into the stance phase. Accordingly, in the hydraulic brake circuit 70, the throttle 94 is effectively operated to provide a flexible knee bending function, i.e., to exhibit a yielding function. And in the stance phase, when the floor reaction force of the wearer is located at the front side of the instantaneous center O of the link mechanism 50 (i.e., when the floor reaction force is shifted to the toe 172t side), the switch valve 60 is surely switched into the open position under the effect of the link mechanism 50. Accordingly, the hydraulic brake circuit 70 does not produce any unnecessary braking force to the knee bending operation and the wearer can smoothly depart the toe of the foot from the floor. Although the switch valve 60 is of a normal closed type, it is brought into the open position by force of inertia caused by swinging out motion of the prosthetic limb 10 in the swing phase. For this reason, the hydraulic brake circuit 70 is not interfered with the controlling operation made by the air cylinder apparatus 30 in the swing phase, in spite of the fact that the switch valve 70 is of a normal closed type.

Figure 7A:
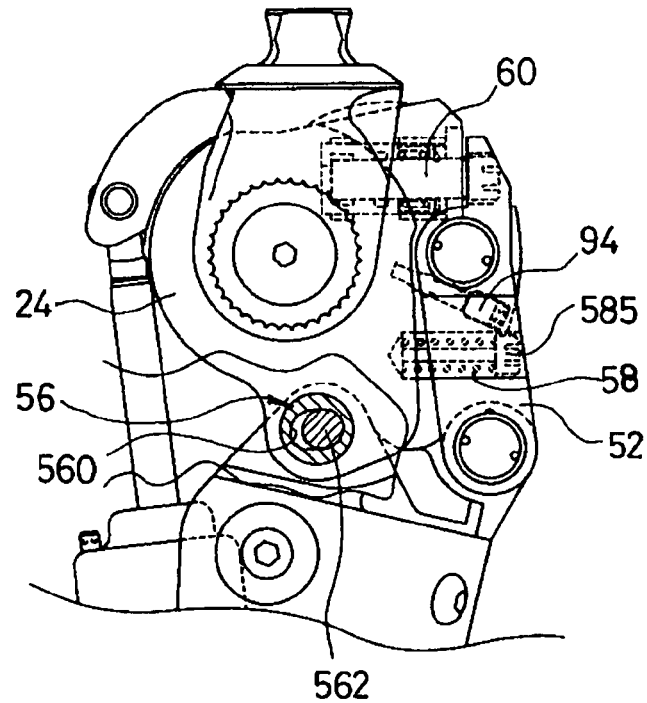
FIG. 7A is a view showing the construction of a part surrounding a knee axis of the embodiment of FIG. 1, in which a switch valve is in a closed position.
Figure 7B:
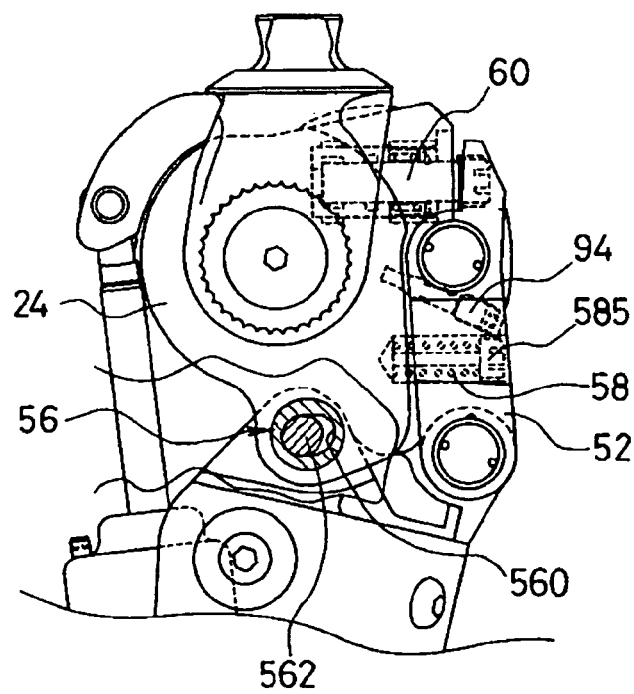
FIG. 7B is a view showing the construction of a part surrounding a knee axis of the embodiment of FIG. 1, in which the switch valve is in an open position.
Figure 8:
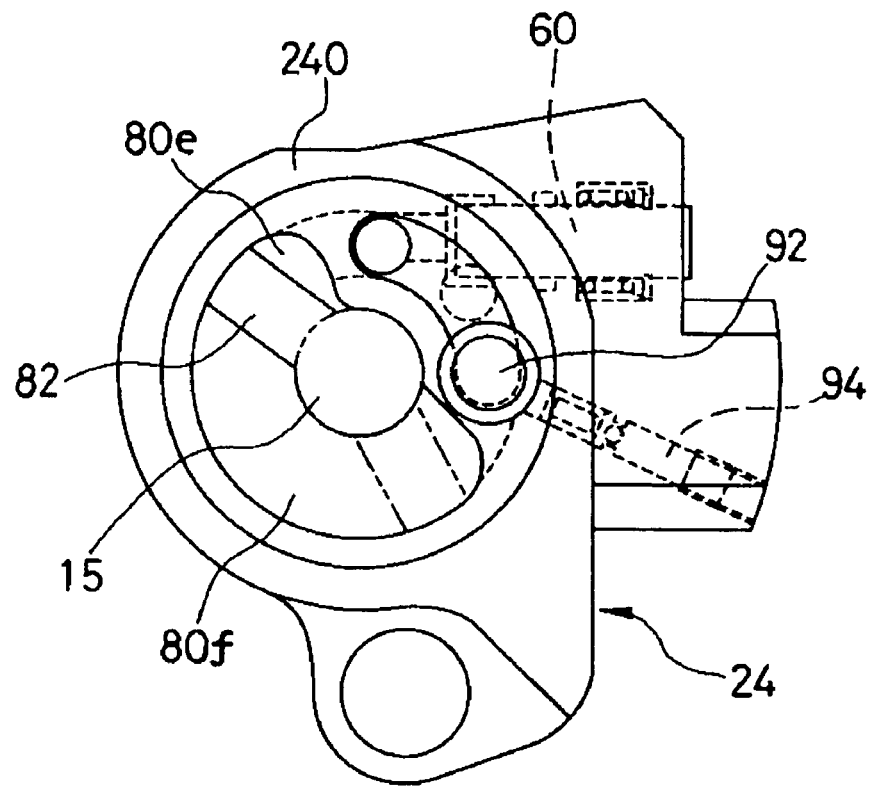
FIG. 8 is a view showing the construction of the inside of a housing member.

The specific construction of the hydraulic brake circuit 70 in the thigh prosthetic limb 10 will now be described. In addition to FIGS. 1 through 3 already referred to, FIGS. 7A and 7B and FIG. 8 are useful in knowing the relation of arrangement of various component elements of the hydraulic brake circuit 70. FIGS. 7A and 7B show the construction of an upper part of the thigh prosthetic limb 10, especially a part surrounding the knee axis. FIG. 7A shows a closed state (i.e., normal state and a state in which the heel 172$h$ side of the foot is contacted with the floor) of the switch valve 60, and FIG. 7B shows an open state (i.e., a state in which the toe 172$t$ side of the foot is contacted with the floor) of the switch valve 60. In the examples shown in those Figures, the front link of the link mechanism 50 is a bar link (front link 52), while the rear link is a slide 56. The slide 56 comprises a guide hole 560 formed in the main body 240 of the housing member 24 and a guide rod 562 guided by the guide hole 560. The guide rod 562 is fixed to the base bracket 22. Accordingly, the housing member 24 having the guide hole 560 and the base bracket 22 integral with the frame 140 can relatively slightly be moved by the link mechanism 50. The amount of the movement is sufficient for switching the switch valve 60 from the closed position to the open position or in the reversed way. For example, the amount of the movement is a stroke equal to several mm or less, or a pivotal angle equal to several degrees or less.

FIG. 8 is a view in which a cover member 242 of the housing member 24 is removed and the main body 240 part of the housing member 24 is viewed from the axial direction of the knee axis. The turnable vane 82 is integrally supported by the knee axis 15 which is fixed to the knee axis support arms 124$a$, 124$b$ of the knee plate 120. The turnable vane 82 partitions the inside space of the main body 240 into the first chamber (high pressure chamber or extending chamber) 80$e$ and the second chamber (low pressure chamber or bending chamber) 80$f$. The main body 240 of the housing member 24 receives therein the switch valve 60, a throttle valve as the throttle 94 and the check valve 92. A receiving part of the switch valve 60 is located at an upper part of the main body 240 and a receiving part of the throttle valve 94 is located at a lower part thereof. A receiving part of the check valve 92 is located at an inner part of the receiving part of the throttle valve 94. The receiving parts of the switch valve 60 and the throttle valve 94 extend toward the inside of the main body from one surface of the main body 240 which faces the front link 52. On the other hand, the receiving part of the check valve 92 extends in a direction parallel to the axial direction of the knee axis 15. Moreover, a passageway of the hydraulic brake circuit 70 is also formed in the main body 240 of the housing member 24.

Figure 9:
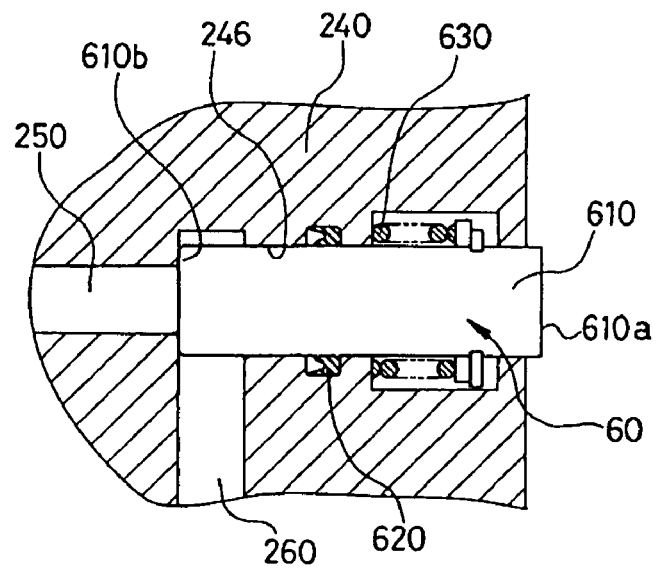
FIG. 9 is a sectional view showing a switch valve receiving in the housing member.

FIG. 9 is a sectional view showing the switch valve 60 received in the main body 240 of the housing member 24. The main body 240 is provided with the first passageway 250 on the high pressure side, the second passageway 260 on the low pressure side and a receiving hole 246 which is communicated with the first and second passageways 250, 260. The switch valve 60 is adapted to intercommunicate or cutoff the communication between the first passageway 250 side and the second passageway 260 side. A main body of the switch valve 60 is a small-sized plunger 610 which is movably fitted to the interior of the receiving hole 246. The plunger 610 is sealed liquid tight by a seal member 620 located at an outer periphery thereof and subjected to force directing outward of the receiving hole 246 which force is produced by a valve spring 630. However, the plunger 610 is also subjected at one end 610$a$, which projects from the receiving hole 246, to force produced by the spring 58 through the front link 52. In order for the force of the spring 58 to overcome the force of the valve spring 630, in a normal condition, a distal end 610$b$ of the plunger 610 is abutted with a valve seat on the main body 240 side, thereby maintaining the switch valve 60 in the closed position. On the other hand, when the link mechanism 50 detects that the toe 172$t$ has contacted with the floor, the force of the spring 58 acting through the front link 52 is canceled and therefore, the plunger 610 is caused to move outward of the receiving hole 246 by the force of the valve spring 630 to bring the switch valve 60 into the open position. As already described previously, since the switch valve 60 produces a ring-like large opening in response to slight movement of the plunger 610, it is switched from the closed position to the open position or from the open position to the closed position rapidly and surely. One end of the spring 58 is retained by the main body 240 of the housing 24 and the other end is retained by a threaded member 585 which is threadingly engaged with the front link 52. Accordingly, by varying the threading amount of the threaded member 585, the force of the spring 58 can be adjusted (see FIGS. 7A and 7B).

Figure 10:
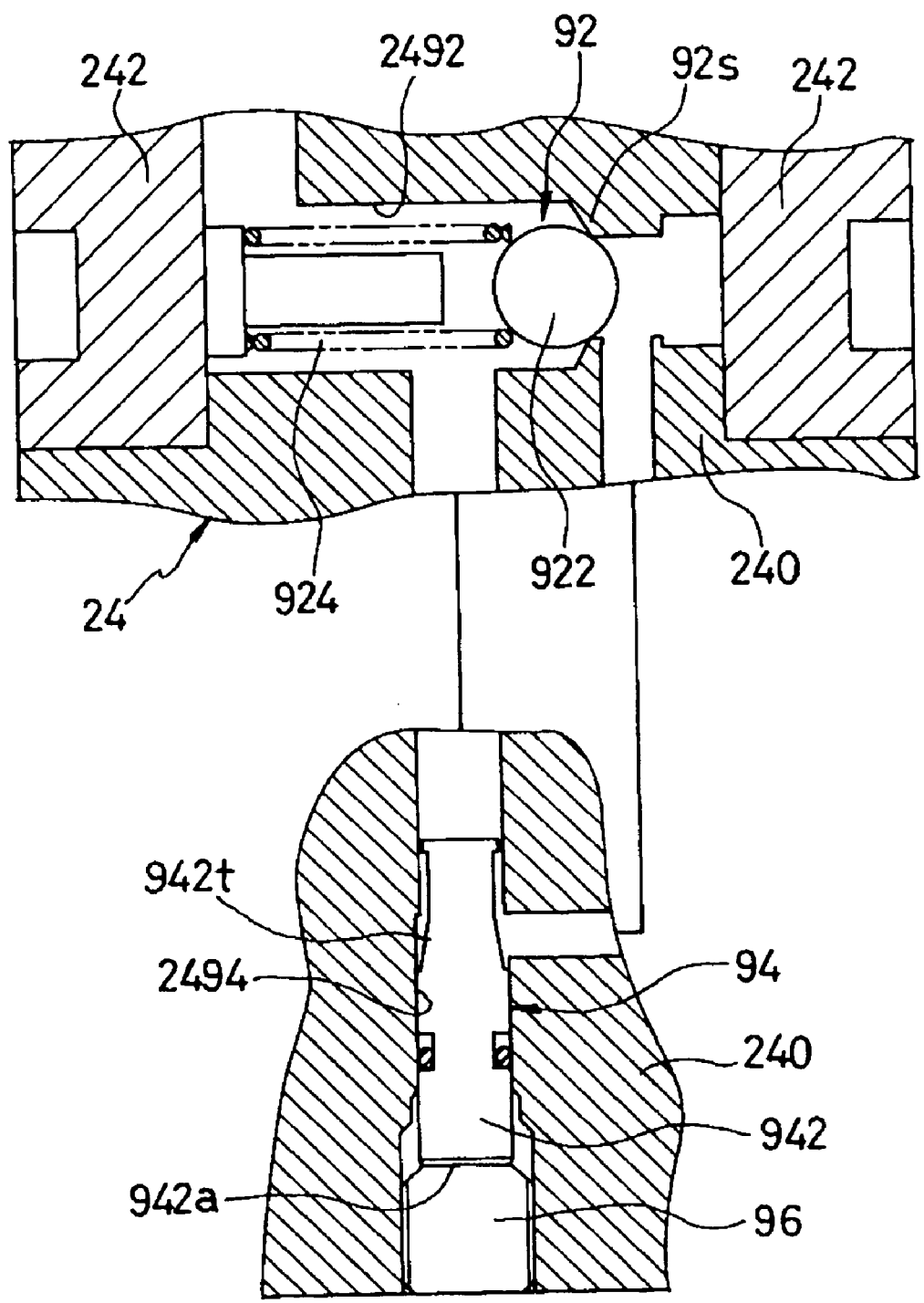
FIG. 10 is a sectional view showing a check valve and a throttle valve received in the housing member.

FIG. 10 is a sectional view showing the check valve 92 and the throttle valve 94 receiving in the housing member 24. The check valve 92 and the throttle valve 94 are arranged in such a manner as to be orthogonal to each other within the housing member 24. A receiving hole 2492 of the check valve 92 laterally pierces through the main body 240 of the housing member 24, and opposite sides of the receiving hole 2492 are closed by cover members 242. The receiving hole 2492 is provided at an intermediate part thereof in the axial direction with an inner wall part 92$s$ which serves as a valve seat of the check valve 92. The check valve 92 includes, in addition to the valve seat 92$s$, a ball valve body 922 sitting on the valve seat 92$s$ and a valve spring 924 for exerting a sitting force to the ball valve body 922. On the other hand, a receiving hole 2494 of the throttle valve 94 diagonally extends through the main body 240 of the housing member 24 and an opening at one end thereof is faced forwardly of the prosthetic limb 10. A main body of the throttle valve 94 is a plunger valve body 942 inserted in the receiving hole 2494. The plunger valve body 942 is provided with cutout grooves 942$t$ (two cutout grooves arranged at an interval of 180 degrees in the peripheral direction and slanted in the axial direction) formed in an outer periphery on one side thereof in the axial direction. Those two cutout grooves 942$t$ with the help of the wall surface of the main body 240 of the housing member 24 produces a flow resistance. That side of the plunger valve body 942 where the cutout groove 942$t$ is formed is located at an inner part of the receiving hole 2494, and an end part 942$a$ on the opposite side is supported by the threaded member 96. Accordingly, by varying the threading amount of the threaded member 96 into the receiving hole 2494 of the main body 240, the throttling amount of the throttle valve 94 can be adjusted. The distal end side of the plunger 92 of the throttle valve 94 where the cutout groove 942$t$ is formed is communicated with the high pressure side of the check valve 92. An outer periphery of each cutout groove 942$t$ is communicated with the low pressure side of the check valve 92. Those communications are achieved by a passageway formed in the main body 240 of the housing member 24.

The throttle valve 94 is demanded to be adjustable in throttling amount after the prosthetic limb 10 is assembled, while there is no such demand for the check valve 92. Thus, the check valve 92 may be disposed within the turnable vane 82 instead of within the housing member 24. The turnable vane 82 is integral with the knee axis 15 and executes such a large turning motion as 150 degrees to 160 degrees which are same as the turning angles of the knee joint. However, the range capable of producing a braking force for the yielding function is only in the range from an extended state of the knee to a bent state achieved by bending the knee at an angle of approximately 90 degrees. Accordingly, in the range from a state in which the knee is bent at 90 degrees to a state in which the knee is bent at maximum angles, the braking force produced by the hydraulic brake circuit 70 is basically not required. In that range, it is preferred that the turnable vane 82 can turn smoothly irrespective of the opening/closing operation of the switch valve 60. For this purpose, it is preferable that a passageway for restraining the production of unnecessary braking force is formed in the main body 240 of the housing member 24.

Figure 11:
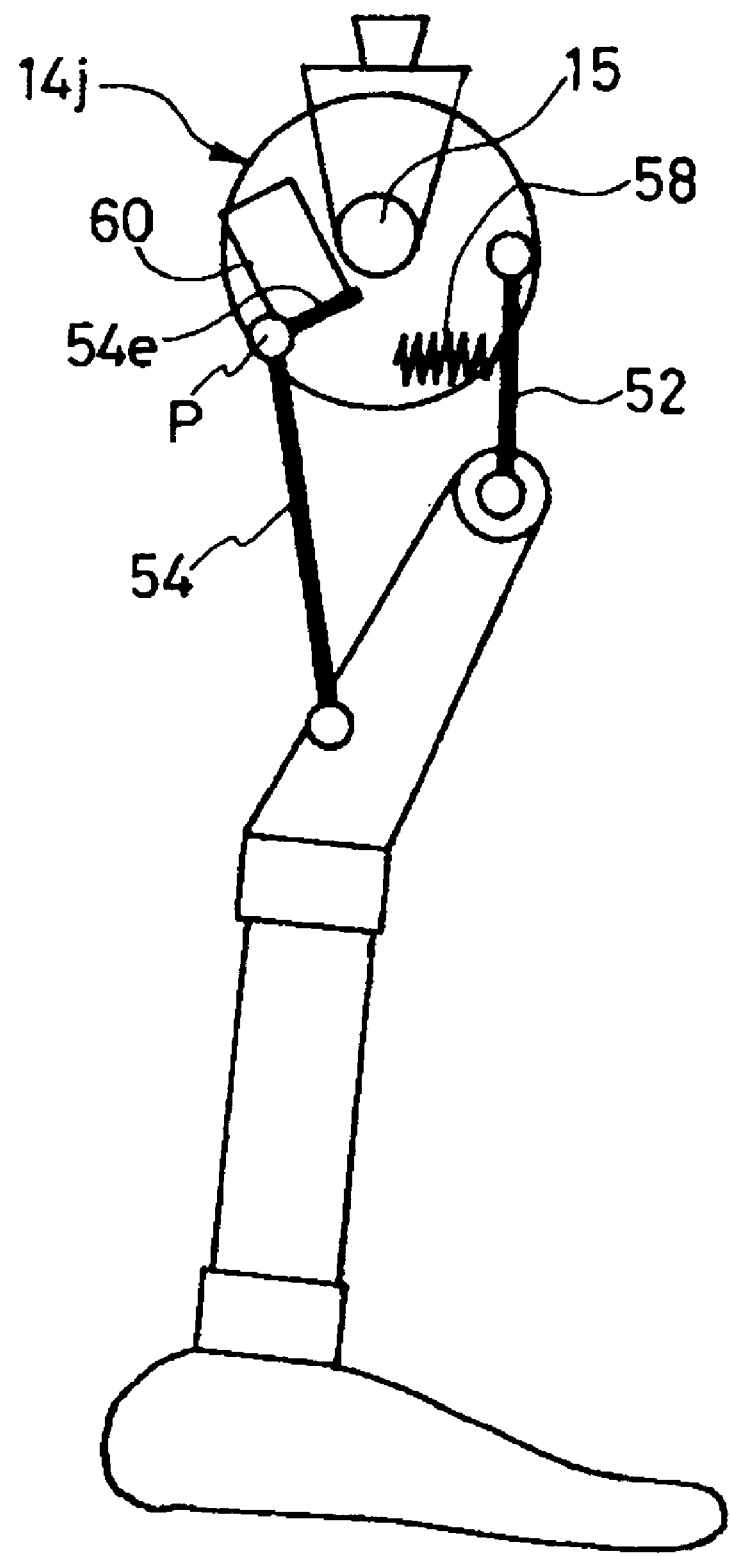
FIG. 11 is a view showing a modified embodiment of the present invention.

The present invention is not limited to the illustrated embodiments. Instead, many modifications can be made within a range not departing from the subject matter, i.e., mechanical sensing is executed, of the present invention. FIG. 11 shows another example, in which the control element of the switch valve 60 is disposed on the rear link 54 side instead of on the front link 52 side. The rear link 54 includes a link part 54e serving as an operating element which is disposed at a pivot joint part P with respect to the housing member 24 which serves as the joint component part 14j.

Figure 12:
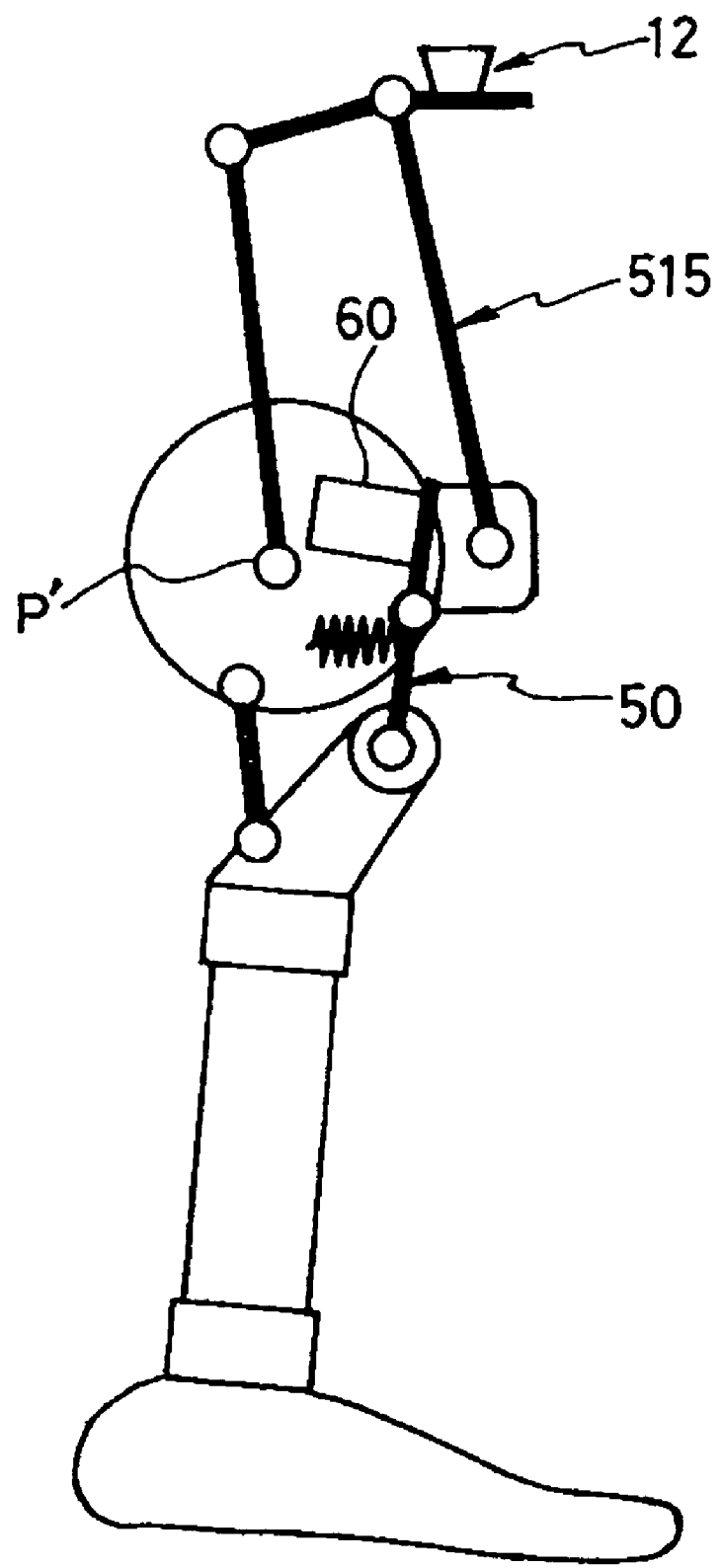
FIG. 12 is a view showing another modified embodiment of the present invention.
Figure 13:
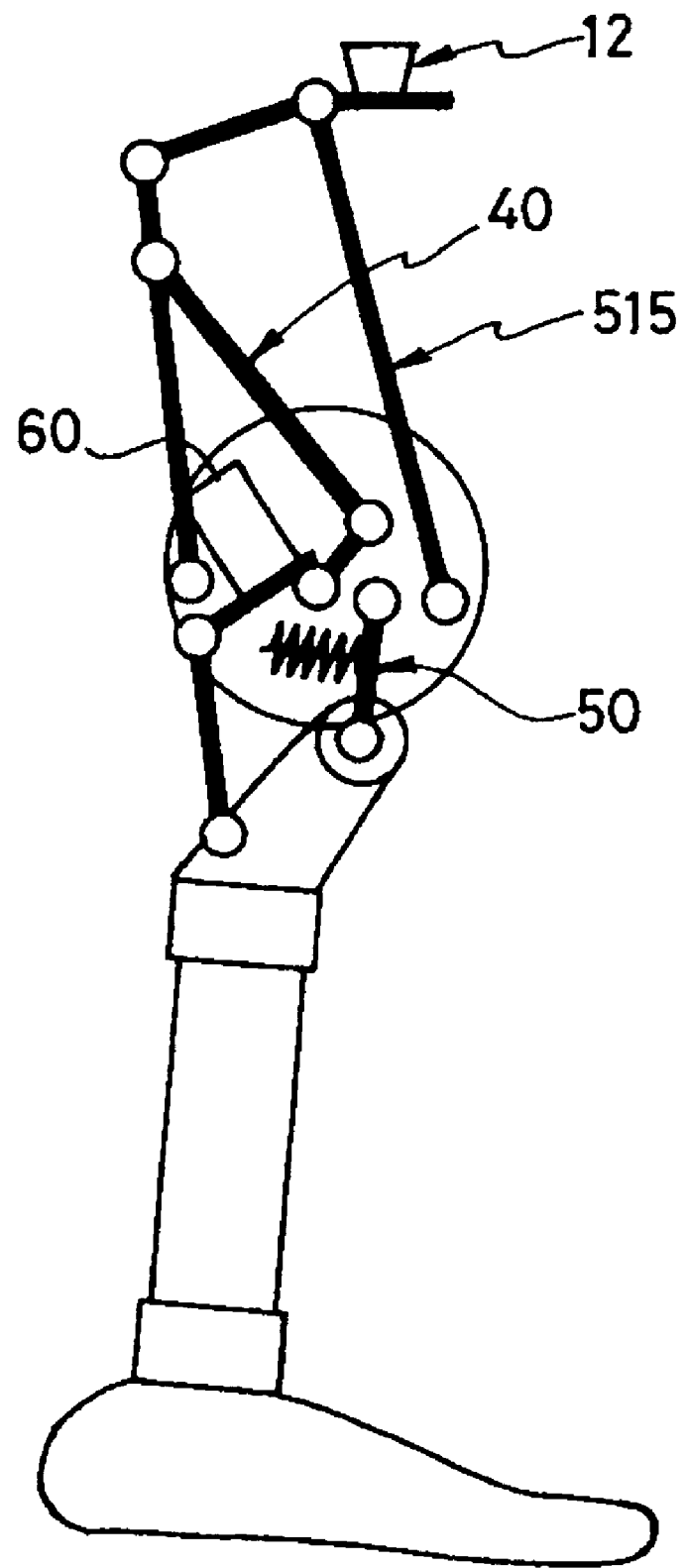
FIG. 13 is a view showing a further modified embodiment of the present invention.

The present invention can be applied not only to a prosthetic limb having a single axis but also to a prosthetic limb having a multi-axis. FIGS. 12 and 13 show examples in which the present invention is applied to a prosthetic limb equipped with a quadratic link mechanism 515 composing the knee joint. In the example of FIG. 12, one pivot joint part P' in the link mechanism 515 is braked. On the other hand, in the example of FIG. 13, a rod 40 is connected to the link mechanism 515 and motion of the link mechanism 515 is braked through the rod 40. Those component parts of FIGS. 12 and 13 which are identical with the component parts in the above-mentioned embodiment are denoted by identical reference numeral.

Figure 14:
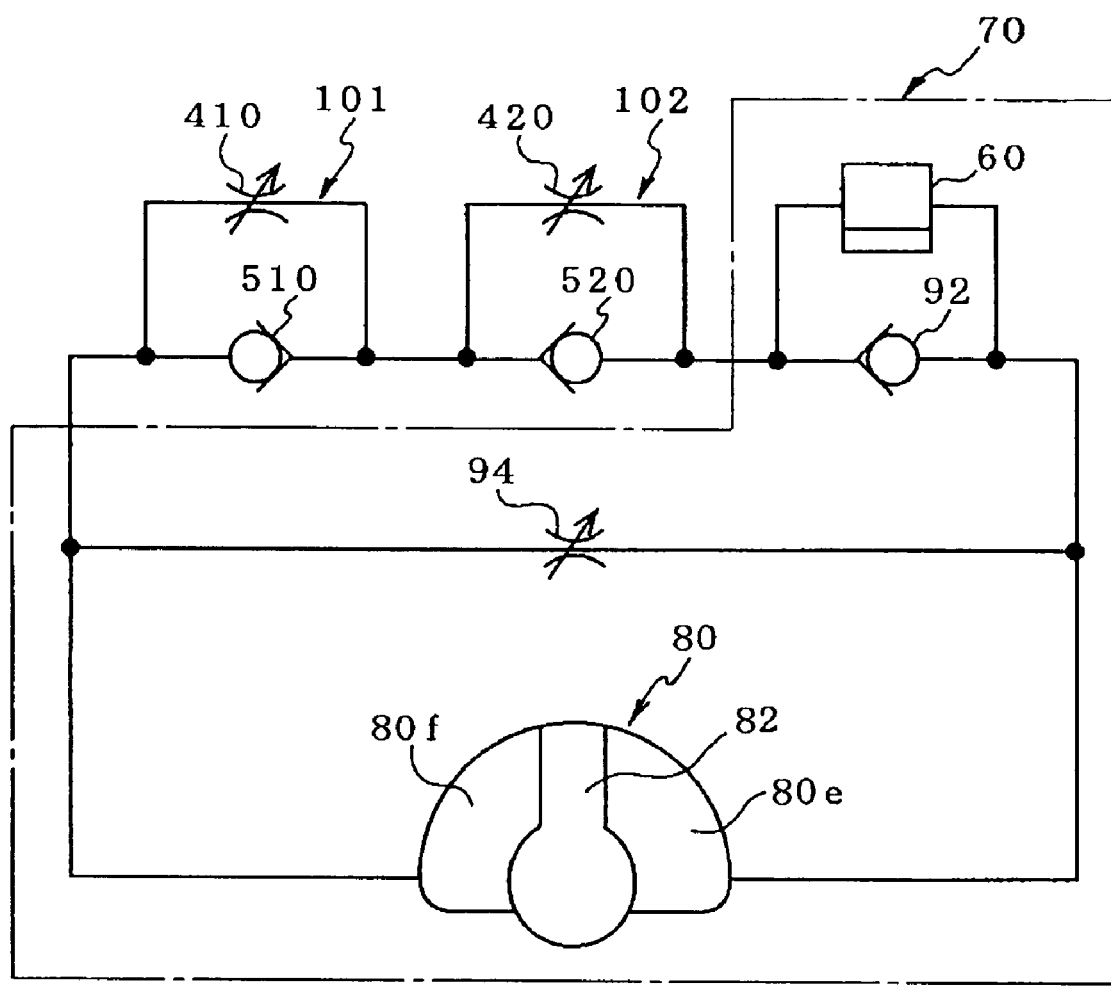
FIG. 14 is a circuit diagram in which another hydraulic circuit is combined instead of a pneumatic circuit of FIG. 6.

FIG. 14 shows a combination circuit in which hydraulic component elements are combined with the knee brake circuit 70 operated by hydraulic and including a switch valve 60. The newly employed component elements which are to be combined with the knee brake circuit 70 are an extending auxiliary circuit 101 including a throttle valve 410 and a check valve 510, and a bending auxiliary circuit 102 including a throttle 420 and a check valve 520. The knee brake circuit 70 is adapted to obtain a flexible knee braking function in a stance phase of the prosthetic limb, while the extending auxiliary circuit 101 and the bending auxiliary circuit 102 are adapted to obtain a flexible knee braking function in a swing phase of the prosthetic limb. Accordingly, the throttles 410, 420 in the extending auxiliary circuit 101 and the bending auxiliary circuit 102 are small in throttling amount compared with the throttle 40 of the knee brake circuit 70. The flow resistance caused by those throttles 410, 420 is a value corresponding to a bending resistance and 8 Nm at the maximum. The check valves 510, 520 in the extending auxiliary circuit 101 and the bending auxiliary circuit 102 are, of course, one-way valves which allow only the mutually reversed flows. In case the controlling operation in a stance phase and in a swing phase is executed by the hydraulic circuit, the hydraulic circuit can be built in a knee part of the prosthetic limb. This makes it possible to design the prosthetic limb smaller in size.

The invention claimed is:

1. A prosthetic limb comprising a knee joint, a joint upper member located above said knee joint and a joint lower member located below said knee joint and both the joint upper member and joint lower member being pivotably connected to one another about said knee joint such that the limb can be bent about said knee joint;

a foot attached to the joint lower member;

wherein said joint lower member includes a component which comprises part of said knee joint and a main body part connected to said component by a connection and said component moves only several mm or less in stroke, or several degrees or less in a pivotal angle in comparison with the bending motion of the main body part said prosthetic limb having the following constitutional features X and Y in order to brake the bending motion of said knee flexibly, X. a hydraulic brake circuit for producing a braking force with respect to the bending motion of the knee by flow resistance generated when a working fluid passes through a throttle said hydraulic brake circuit comprises said throttle which generates flow resistance, and a switch valve which switches the throttling function of the throttle between effective state and ineffective state, and Y. sensing control means for detecting which part of the foot attached to said prosthetic limb the weight of the wearer is imposed on and generating a detection signal to control the switch valve in said hydraulic brake circuit in accordance with the detection signal; and said sensing control means has the following features y1 and y2, y1. a link mechanism for connecting said component and said main body part to each other in said joint lower member and having an instantaneous center between a toe and a heel of said foot of said prosthetic limb, wherein a first link in said link mechanism is an operating member to switch the switch valve; and y2. motion of said first link constituting said link mechanism moves said switch valve to switch the throttling function of said throttle between effective state and ineffective state.

2. A prosthetic limb according to claim 1, wherein said sensing control means comprises a sensing part for detecting which part of said foot the load of the wearer is imposed on, and a control means for controlling said switch valve in said hydraulic brake circuit in accordance with the detection signal coming from said sensing part.

3. A prosthetic limb according to claim 2, wherein said sensing part is of a mechanical construction.

4. A prosthetic limb according to claim 1, wherein the connection for pivotably connecting said joint upper member and said joint lower member together is a connection by means of either a single-axis using only one axis or a multi-axis using plural axes.

5. A prosthetic limb according to claim 1, wherein said hydraulic brake circuit, when controlled by said sensing control means, can be switched between a braking position for producing a braking force with respect to the bending motion of the knee and a non-braking position where the braking force is canceled.

6. A prosthetic limb according to claim 5, wherein said hydraulic brake circuit is mechanically controlled in accordance with motion of said first link composing said link mechanism, and said motion of several mm or less in stroke, or several degrees or less in a pivotal angle, between said component and said main body part is sufficient to switch said hydraulic brake circuit between the braking position and the non-braking position.

7. A prosthetic limb according to claim 1, wherein said hydraulic brake circuit includes a first chamber into which a working fluid flows when the knee is extended, a second chamber into which a working fluid flows when the knee is bent, a passageway for intercommunicating said first and second chambers, said throttle located between said first chamber and said second chamber on said passageway and for applying a braking force to the bending motion of the knee utilizing a flow resistance of the working fluid which passes through said throttle, a check valve connected, in parallel, to said throttle on said passageway and adapted to prohibit a flow from said first chamber to said second chamber and allow a flow in the opposite direction, and said switch valve connected, in parallel, to said check valve and said throttle on said passageway and opened/closed by said sensing control means.

8. A prosthetic limb according to claim 7, wherein said switch valve is a seat valve which can be opened/closed by urging a valve body against a valve seat, and said valve body moves in a direction orthogonal to a plane of said valve seat when the valve is opened/closed.

9. A prosthetic limb according to claim 7, wherein said first and second chambers are partitioned by either a vane which is pivotable about one point or a piston which is linearly reciprocally movable.

10. A prosthetic limb according to claim 7, wherein the first link for controlling said hydraulic brake circuit normally closes said switch valve under the effect of a spring.

11. A prosthetic limb according to claim 1, wherein said braking force is in such magnitude that the knee joint is slowly changed in bending angle by imposing the load of the wearer himself/herself thereon when the prosthetic limb is in a stance phase.

12. A prosthetic limb according to claim 1, wherein said sensing control means controls said hydraulic brake circuit in the following manner, z1. when the heel of the foot of said prosthetic limb is contacted with the floor, a floor reaction force caused by grounding of the heel passes through a rear side of the instantaneous center of said link mechanism, thereby generating a rotational moment to said joint lower member in a forwardly folding direction about the instantaneous center, z2. when the toe of the foot of said prosthetic limb is contacted with the floor, a floor reaction force caused by grounding of the toe passes through a front side of the instantaneous center of said link mechanism, thereby generating a rotational moment to said joint lower member in a backwardly folding direction about the instantaneous center, and z3. switching is made between a braking position where a braking force is produced with respect to the bending motion of the knee and a non-braking position where the braking force is canceled, by controlling said hydraulic brake circuit depending on the direction of said rotational moment in z1 and z2.

13. A prosthetic limb according to claim 1, wherein said instantaneous center is located closer to the toe side than to the heel side of the foot.

14. A prosthetic limb according to claim 1, wherein said hydraulic brake circuit is disposed at said component, and said prosthetic limb further comprises an air cylinder disposed between said joint upper member and said joint lower member and adapted to assist the bending motion and the extending motion of the knee in the swing phase.

15. A prosthetic limb according to claim 1, wherein said hydraulic brake circuit makes it possible to bend the knee joint by imposing the load of the wearer himself/herself thereon when said prosthetic limb is in the stance phase, and said prosthetic limb further comprises a hydraulic control circuit for assisting the bending motion and the extending motion of the knee in the swing phase.

* * * * *